(12) United States Patent
Alkemade et al.

(10) Patent No.: US 7,309,415 B2
(45) Date of Patent: Dec. 18, 2007

(54) GAS SENSOR AND METHOD FOR MEASURING A GAS COMPONENT IN A GAS MIXTURE

(75) Inventors: Ulrich Alkemade, Leonberg (DE); Bernd Schumann, Rutesheim (DE); Berndt Cramer, Leonberg (DE); Marget Schuele, Weil der Stadt (DE); Thorsten Ochs, Schwieberdingen (DE); Sabine Thiemann-Handler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 747 days.

(21) Appl. No.: 10/467,647

(22) PCT Filed: Feb. 5, 2002

(86) PCT No.: PCT/DE02/00402

§ 371 (c)(1),
(2), (4) Date: Jan. 21, 2004

(87) PCT Pub. No.: WO02/065113

PCT Pub. Date: Aug. 22, 2002

(65) Prior Publication Data

US 2004/0112765 A1 Jun. 17, 2004

(30) Foreign Application Priority Data

Feb. 10, 2001 (DE) ................ 101 06 171

(51) Int. Cl.
*G01N 27/04* (2006.01)
(52) U.S. Cl. .............. 205/781; 204/425; 204/426; 205/784.5

(58) Field of Classification Search ......... 205/781, 205/783.5–785; 204/424–429; 73/23.31, 73/23.32
See application file for complete search history.

(56) References Cited

U.S. PATENT DOCUMENTS

| 5,893,968 | A | | 4/1999 | Kato |
| 5,997,707 | A | * | 12/1999 | Kato et al. ............ 204/425 |
| 6,325,906 | B1 | * | 12/2001 | Kitanoya et al. ....... 204/425 |
| 6,338,783 | B1 | * | 1/2002 | Inoue et al. .......... 204/425 |
| 6,637,197 | B1 | * | 10/2003 | Stahl ................. 60/295 |

FOREIGN PATENT DOCUMENTS

| DE | 69225838 | 11/1998 |
| EP | 0 241 751 | 10/1987 |

(Continued)

OTHER PUBLICATIONS

English Language Abstract of EP 0 241 751.

*Primary Examiner*—Nam Nguyen
*Assistant Examiner*—Surekha Vathyam
(74) *Attorney, Agent, or Firm*—Kenyon & Kenyon LLP

(57) ABSTRACT

A gas sensor based on solid electrolyte is proposed for measuring a gas component in a gas mixture, having at least one sensitive region, which has a first means for producing a reaction gas from an additional gas component of the gas mixture. A second means is situated in the sensitive region of the gas sensor, using which the residual content of the reaction gas may be determined, after a reaction that takes place between the reaction gas and the gas component to be measured.

25 Claims, 5 Drawing Sheets

FOREIGN PATENT DOCUMENTS

| | | |
|---|---|---|
| EP | 0 517 364 | 12/1992 |
| EP | 0798555 | 3/1997 |
| EP | 1 006 354 | 6/2000 |
| JP | 2000088800 | 3/2000 |
| WO | 00 71870 | 11/2000 |
| WO | 01 02845 | 1/2001 |

* cited by examiner

GAS SENSOR AND METHOD FOR MEASURING A GAS COMPONENT IN A GAS MIXTURE

FIELD OF THE INVENTION

The present invention relates to a gas sensor and a method for measuring a gas component in a gas mixture.

BACKGROUND INFORMATION

In the course of progressive environmental legislation, the demand is growing for sensors that allow even the smallest quantities of pollutants may be reliably determined. In this context, above all, gas sensors play a great role which make possible the determination of gaseous pollutants in the ppm range, independent of the temperature of the measuring gas. The measuring signals of the gas sensor proportional to the quantity of pollutant are, in this connection, often so small that great measuring inaccuracy may not be avoided. A possible way out of this dilemma is represented by an indirect determination of pollutants.

Thus, a gas sensor disclosed in European Patent Application No. 241 751 monitors the content of ammonia, carbon monoxide, hydrocarbons, nitrogen oxides or sulfur dioxide in gas mixtures, but not the oxygen content. To be able to determine nitrogen oxides, among other things, a measuring method is proposed in which a known quantity of ammonia is added to a gas mixture as reaction gas which reacts with the nitrogen oxides at a catalyst of the gas sensor. If the quantity of ammonia originally added is known, one may conclude what the NOx concentration in the gas mixture is, by determining the remaining content of ammonia. The disadvantage of this method is that a device for adding the ammonia has to be provided.

It is the object of the present invention to make available a gas sensor which makes possible measuring various gas components in a gas mixture, reliably and using accurate timing.

SUMMARY OF THE INVENTION

The gas sensor and method according to the present invention provides indirect determination of the gas component to be measured, via the determination of the remaining contents of a reaction gas, after the latter has fully reacted with the gas component to be measured. It is of advantage that the reaction gas does not first have to be added to the gas mixture, which would require one or possibly more appropriate devices, but that it is generated in the gas sensor itself.

For this purpose, the gas sensor has a first means by which, in a first step, a reaction gas is produced from another gas component of the gas mixture which is not the gas component to be measured. This reacts, in a second step, with the gas component to be measured. The gas sensor also includes a sensitive region, in which a second means is situated which, in a third step, permits the determination of the residual content of reaction gas after its reaction with the gas component to be measured. If the reaction gas is generated in excess in comparison to the gas component to be measured, and if the quantity of generated reaction gas is known, one may conclude from the residual content of reaction gas what the quantity of gas component to be measured originally was in the gas mixture.

It is advantageous if an electrochemical pumping cell is provided as the first means, at whose electrode facing the gas mixture the further gas component may be reduced or oxidized as needed while forming a reaction gas. As the second means, depending on the particular application, an electrochemical pump cell, an electrochemical concentration cell or a resistive measuring element may be implemented.

Furthermore, it is advantageous if a catalyst is provided in the gas sensor, which catalyzes the reaction of the gas component to be measured and the reaction gas. The catalyst may cover an extent of one of the electrodes of the first or second means.

In an embodiment of the present invention, an electrochemical pump cell is connected upstream of the first and second means, which has the effect of regulating the oxygen proportion in the gas mixture before it reaches the sensitive region of the gas sensor. If the electrochemical pump cell is combined with an electrochemical concentration cell, this increases the accuracy with which the oxygen proportion of the gas mixture may be regulated, and at the same time makes possible the additional determination of the oxygen proportion in the gas mixture. The regulation of the oxygen proportion takes place, for example, in a first region of a measuring gas chamber of the gas sensor, and the reaction of the gas component to be measured with the reaction gas as well as the determination of the residual content of reaction gas takes place in a second region of the measuring gas chamber.

The determination of the gas component to be measured advantageously takes place in such a way that first a reaction gas is generated from another gas component of the gas mixture, and the gas component to be measured is made to react with the reaction gas within the gas sensor. In this context, the reaction gas should be present in excess with respect to the quantity of the gas component to be measured. After the reaction, the residual content of the reaction gas is determined, and from the residual content one may conclude what the original concentration of the component to be measured was, knowing the quantity of reaction gas just generated.

DETAILED DESCRIPTION

Figure 1:
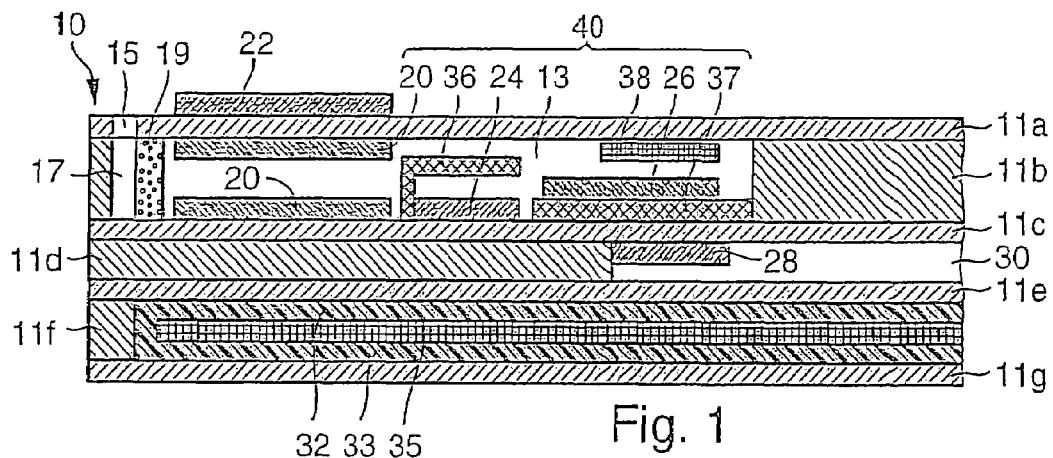
FIG. 1 shows a cross section through the large surface of a sensor element according to a first exemplary embodiment of the present invention.

FIG. 1 shows a basic design of a first specific embodiment according to the present invention. Designated by reference numeral 10 is a planar sensor element of an electrochemical gas sensor, which, for example, has a plurality of solid electrolyte layers 11a, 11b, 11c, 11d, 11e, 11f and 11g that conduct oxygen ions. In this context, solid electrolyte layers 11a-11g are designed as ceramic foils and form a planar ceramic body. The integrated form of the planar ceramic body of sensor element 10 is produced in a manner known per se, by laminating together the ceramic foils printed over with functional layers and subsequently sintering the laminated structure. Each of the solid electrolyte layers 11a through 11g is formed from solid electrolyte material that conducts oxygen ions, such as $ZrO_2$ stabilized partially or fully with $Y_2O_3$. Solid electrolyte layers 11a-11g alternatively may be replaced, at least partially, by foils made of aluminum oxide, at places at which ion conduction in the solid electrolyte is not important or undesired.

Sensor element 10 includes a measuring gas chamber 13, which, via a gas intake port 15, is in contact with a gas mixture surrounding the gas sensor. Gas intake port 15 is designed, for example, as a bore penetrating solid electrolyte layer 11a, but it may also be situated in the same layer plane 11b as measuring gas chamber 13. Between gas intake port 15 and measuring gas chamber 13, and in the direction of diffusion of the measuring gas, a buffer chamber 17 and a diffusion barrier 19 made of porous ceramic material are provided. Buffer chamber 17 is used to avoid signal spikes in the case of rapidly changing gas concentrations in the gas mixture.

In a further layer plane 11d of the sensor element, a reference gas channel 30 is formed, which holds a reference gas atmosphere. The reference gas atmosphere may be air, for example. For this purpose, reference gas channel 30 has an opening, not shown, on the side of the sensor element facing away from the measuring gas, which ensures gas exchange with the surrounding air.

Also, embedded in the ceramic base of sensor element 10, between two insulating layers 32, 33 is a resistance heater 35. The resistance heater is used for heating up sensor element 10 to a necessary operating temperature.

In first measuring gas chamber 13, one or two first inner electrodes 20 are situated. At the outer side of solid electrolyte layer 11a, which directly faces the gas mixture, there is an outer electrode 22, which may be covered by a porous protective layer (not shown). Electrodes 20, 22 form a first electrochemical pump cell. The operating procedure as pump cell includes applying a voltage between electrodes 20, 22 of the pump cell, which results in an ion transport between electrodes 20, 22 all the way through solid electrolyte 11a. The number of the "pumped" ions is directly proportional to a pump current flowing between electrodes 20, 22 of the pump cell.

In measuring gas chamber 13, a second and a third inner electrode 24, 26 are provided downstream from electrode 20 in the diffusion direction of the measuring gas. The common outer electrode which goes with them, which acts as reference electrode 28, is located in reference channel 30. In this context, second inner electrode 24 together with reference electrode 28 forms a second electrochemical pump cell, and third inner electrode 26 together with reference electrode 28 forms a third electrochemical pump cell. In addition, inner electrode 20 may be connected together with reference electrode 28 to form an electrochemical Nernst or concentration cell. By a Nernst cell or a concentration cell, it is generally understood to refer to a two-electrode system in which the two electrodes 20, 28 are exposed to different gas concentrations, and the difference of the potentials present at electrodes 20, 28 is measured.

According to the Nernst equation, this potential difference permits making an inference on what the gas concentrations are at electrodes 20, 28.

A further possibility is connecting second inner electrode 24 to outer electrode 22 to form a second electrochemical pump cell and connecting third inner electrode 26 to outer electrode 22 to form a third electrochemical pump cell.

The electrode material for all electrodes is applied in a generally known way as cermet in order to sinter the electrode material to the ceramic foils.

In order to operate sensor element 10 as gas sensor, the first pump cell is drawn upon, together with the concentration cell for regulating the oxygen proportion of the gas mixture that has diffused into measuring gas chamber 13. A constant partial pressure of oxygen of, for instance, 0.1 through 1000 ppm is set in measuring gas chamber 13 by pumping in or pumping out oxygen. Control of the partial pressure of oxygen in measuring gas chamber 13 is carried out by the concentration cell. In this context, the pump voltage at the pump cell is varied in such a way that, between electrodes 20, 28 of the concentration cell, a constant potential difference sets in. In this context, the pump current flowing in the pump cell is a measure of the oxygen concentration present in the gas mixture that is diffusing in, and makes possible the additional function of the gas sensor as an oxygen probe. Since premature decomposition of the gas component to be measured is undesirable at first inner electrode 20, first inner electrode 20 may be made of a catalytically inactive material, such as gold or a gold-platinum alloy. If the application of the gas sensor is limited to determining stable gas components, inner electrode 20 mentioned may also have in it platinum, a rhodium-platinum alloy or another suitable material.

If the gas mixture present has only a low oxygen proportion, one can do without the first inner electrode and consequently also the first electrochemical pump cell. This is the case, for example, in exhaust gases of motor vehicles which are constantly operated having a lambda value=1. The sensor construction is thereby made simpler.

The gas mixture in measuring gas chamber 13, which is set to a constant oxygen partial pressure, now reaches sensitive region 40 of the gas sensor. In this region, second inner electrode 24 of the second pump cell is situated. At second inner electrode 24, which may, but not necessarily, also has a catalytically inactive material, such as gold or a gold-platinum alloy in it, by applying an appropriate voltage, a reaction gas is generated from an additional gas component of the gas mixture, which is not the gas component to be measured, and this is reacted with the gas component to be measured. If the gas sensor is being used, for example, for determining nitrogen oxides, a potential such as −500 to −750 mV is set with respect to reference electrode 28 at second inner electrode 24, and water and carbon dioxide are reduced to hydrogen and carbon monoxide. The oxygen set free in this context is reduced electrochemically and pumped off.

$$H_2O+2e^- \Leftrightarrow H_2+O^{2-}_{(pumped\ off)} \quad (e^-=electron) \quad (1)$$

$$CO_2+2e^- \Leftrightarrow CO+O^{2-}_{(pumped\ off)} \quad (2)$$

Second electrode 24 is dimensioned so that the generated reaction gas (hydrogen and carbon monoxide) is present in excess with respect to the quantity of gas components (nitrogen oxides) to be measured, contained in the gas mixture. In order to avoid having the gas component to be measured (nitrogen oxides) decomposed too, on account of the strong negative potential of second inner electrode 24, and consequently no longer being available for being measured, second inner electrode 24 may be provided with a protective device 36. As shown in FIG. 1, protective device 36 may be formed, for example from solid electrolyte material or another suitable type of ceramic material. The geometrical design of protective device 36, in the form of a cover layer that is slotted or furnished with a hole, has the effect that only a small part of the gas mixture that has diffused in comes into contact with second inner electrode 24. Since even this small part of the gas mixture has a sufficiently high proportion of the additional gas components (water, carbon dioxide), an excess of reaction gas can nevertheless always be made available. Gas mixtures which contain air, for example, or exhaust gases of internal combustion engines, satisfy this assumption.

The gas mixture enriched with the reaction gas (hydrogen and carbon monoxide) now reaches a part of sensitive region 40 facing away from gas intake port 15. There, in measuring gas chamber 13, a catalyst 38 is applied in the form of a catalytically active layer, which catalyses the reaction of the reaction gas (hydrogen and carbon monoxide) with the gas component to be measured (nitrogen oxides) according to equations (3), (4).

$$xH_2+NO_x \Leftrightarrow xH_2O+1/2N_2 \quad (3)$$

$$xCO+NO_x \Leftrightarrow xCO_2+1/2N_2 \quad (4)$$

Since the reaction gas is present in excess, the complete reaction of the gas component to be measured is ensured. On the side of sensitive region 40 facing away from gas intake port 15, there is also situated a third inner electrode 26, which forms the third pump cell together with reference electrode 28. Third inner electrode 26 may optionally be mounted on an additional solid electrolyte layer 37, in order to shorten the diffusion path between catalyst 38 and third inner electrode 26.

The potential of inner electrode 26 is selected so that oxygen from reference gas channel 30 is pumped to third inner electrode 26 and reacts there with the remaining reaction gas. Since, in this reaction, the reverse reaction of the reaction represented by equations (1), (2) is involved, the additional gas component (water and carbon dioxide) reforms (equations (5), (6)). For this, a potential of −300 to −500 mV is set at third inner electrode 26.

$$H_2+O^{2-} \Leftrightarrow H_2O+2e^- \quad (5)$$

$$CO+O^{2-} \Leftrightarrow CO_2+2e^- \quad (6)$$

Third inner electrode 26 is made of a catalytically active material, such as platinum or an alloy of platinum, rhodium and/or palladium. The pump current flowing in the third pump cell is determined, and is directly proportional to the residual concentration of the reaction gas. Since the initial concentration, originally produced at second inner electrode 24, of the reaction gas in the gas mixture is approximately constant, and may be simply determined by a calibrating measurement, one may draw a conclusion on the original content of the gas component to be measured present in the gas mixture, from the difference of the initial concentration and the residual concentration. The smaller the measured residual concentration of the reaction gas is, the greater the original concentration of the gas component to be measured present in the gas mixture.

The application of a gas sensor having sensor element 10 is not limited to the determination of nitrogen oxides. Basically, reaction gases may be produced either by electrochemical reduction or oxidation, using the second pump cell. In the first case, reduceable gas components may be determined, and in the second case oxidizable ones.

If a reducing potential is set at second inner electrode 24 of the second pump cell, not only hydrogen and carbon monoxide may be produced as reaction gases, but in principle also nitrogen monoxide from nitrogen dioxide, or sulfur monoxide from sulfur dioxide or trioxide.

$$NO_x+2xe^- \Leftrightarrow NO+xO^{2-}_{(pumped\ off)} \quad (7)$$

$$SO_x+2xe^- \Leftrightarrow SO+xO^{2-}_{(pumped\ off)} \quad (8)$$

The reaction gases produced according to equations (7), (8) may be reacted with reduceable gas components, and consequently drawn upon for their determination. The selection of the reaction gas suitable for an individual case depends on the electrochemical standard potentials of the redox reactions running during the production and reaction of the reaction gas, and also on reaction-kinetic criteria.

Measuring oxidizable gas components is also possible, without any change being necessary in the specific embodiment of the gas sensor. Only the potential of second inner electrode 24 is now selected, so that one or more gas components of the gas mixture may be selectively oxidized at suitable temperatures. These may be, for instance, water, nitrogen monoxide, sulfur monoxide or sulfur dioxide.

$$N_2+2O^{2-} \Leftrightarrow 2NO+4e^- \quad (9)$$

$$NO+O^{2-} \Leftrightarrow NO_2+2e^- \quad (10)$$

$$SO+xO^{2-} \Leftrightarrow SO_x+2xe^- \quad x=1,2 \quad (11)$$

$$2O^{2-} \Leftrightarrow O_2+2e^- \quad (12)$$

At catalyst 38 a reaction then takes place of the reaction gas acting in oxidizing fashion with the gas reducing components to be determined, such as ammonia, hydrogen, methane or hydrocarbons.

$$3O_2+CH_4 \Leftrightarrow CO_2+2H_2O \qquad (13)$$

$$3NO_2+4NH_3 \Leftrightarrow 6H_2O+3.5N_2 \qquad (14)$$

$$2NO_2+CH_4 \Leftrightarrow CO_2+2H_2O+N_2 \qquad (15)$$

In order to be able to determine the residual content of the oxidizing acting reaction gas at third inner pump electrode 26, the potential of this electrode with respect to reference electrode 28 is selected in such a way that the residual content of reaction gas at third pump electrode 26 is reduced and the oxygen being liberated in the process is pumped off into reference gas channel 30. The pump current now appearing with an opposite sign is utilized as the measuring signal. From the difference of the initial concentration present at first and the residual concentration of the reaction gas remaining after the reaction, one may come to a conclusion as to the original concentration of the gas component to be measured in the measuring gas. Thus, depending on the selection of the potentials at inner electrodes 24, 26, the present gas sensor is suitable for determining both reducing and oxidizing gas components of a gas mixture.

If a reducing potential is set at second inner electrode 24 and an oxidizing potential is set at third inner electrode 26, oxidizing gas components may be determined, using the gas sensor. If an oxidizing potential is set at second inner electrode 24 and a reducing potential is set at third inner electrode 26, reducing gas components may be determined. In this context, the second inner electrode has a selective effect with regard to the production of oxygen, and prevents oxidation of the detectable gas components.

By fine tuning the oxidizing and reducing potential at second inner electrode 24, selectively determined oxidizing or reducing reaction gases, or mixtures of various oxidizing or reducing reaction gases may be produced. The potentials to be set for this, taking into consideration possible overvoltages, come about from the standard potentials of the reactions, in which the reaction gases are formed from additional gas components.

Since the potentials present at electrodes 24, 26 may be varied quickly, there is also the possibility of determining, periodically or at short time intervals, one or more reducing or oxidizing gas components, alternatingly one after another, using one sensor.

In another embodiment it is provided that second inner electrode 24 is contacted by a constant current source, a large electrical resistor, for example, in comparison to the electrical resistance of second inner electrode 24 being provided between current source and electrode 24, in such a way that the predominant part of the electric voltage present at the electrical resistor and at electrode 24 falls off at the electrical resistor.

Since the quantity of the reaction gas produced at second inner electrode 24 is a function of the electrode current of electrode 24, applying a constant current makes it possible to make available a constant volume of reaction gas per unit of time. To make possible an operation of the sensor element that is as effective as possible, it is useful, on the one hand, to select the potential applied to second inner electrode 24 so that the electrochemical production of the desired reaction gas from an additional gas component is ensured, and, on the other hand, to limit the electrode current at electrode 24 in such a way that the reaction gas produced is present in slight excess with respect to the gas component to be measured. In this way, the sensor signal of the sensor element becomes independent of the concentration of additional gas components from which the reaction gas is produced at second inner electrode 24.

Figure 2:
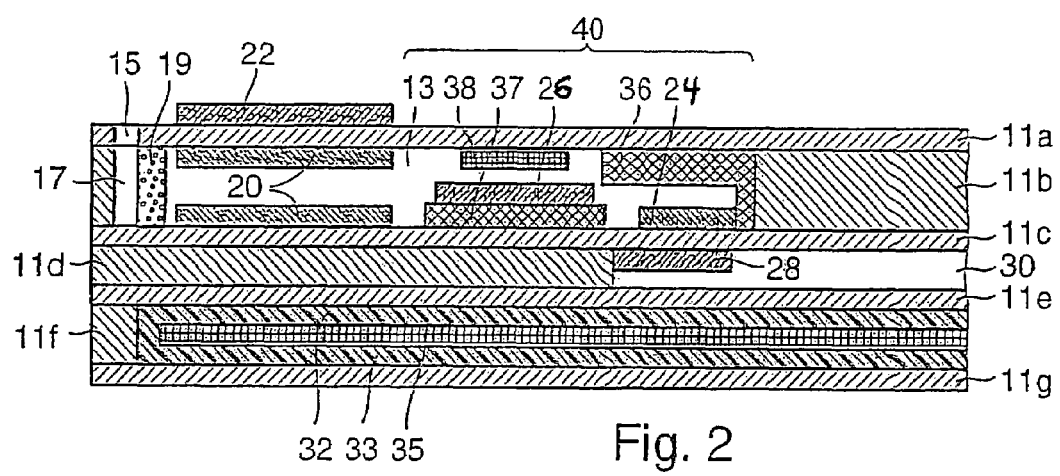
FIG. 2 shows a cross section through the large surface of a sensor element according to a first variant of the first exemplary embodiment, in which the positions of first and second means and catalyst are interchanged.
Figure 3:
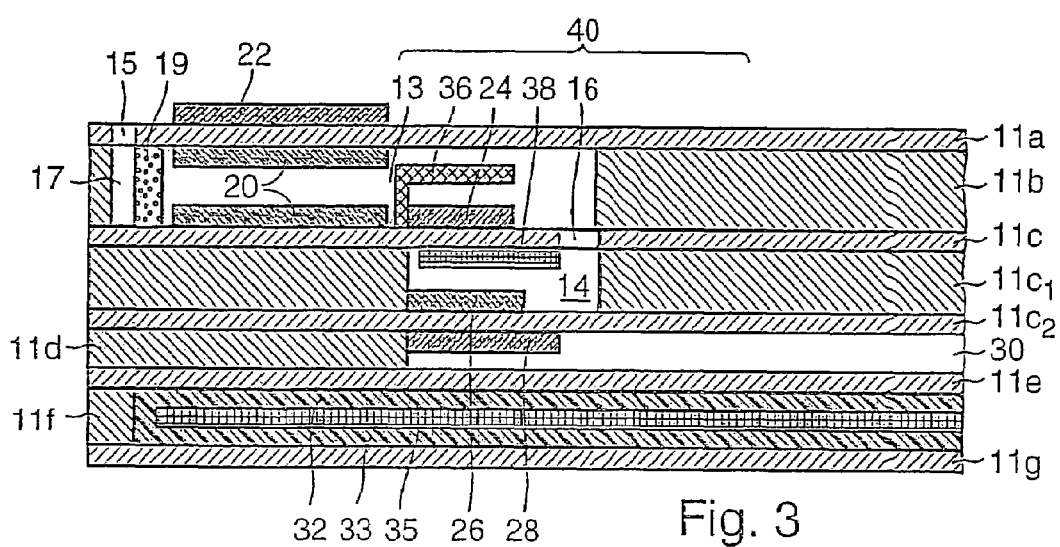
FIG. 3 shows a cross section through the large surface of a sensor element according to a second variant of the first exemplary embodiment, the second means and the catalyst being situated in a separate layer plane of the gas sensor.
Figure 4:
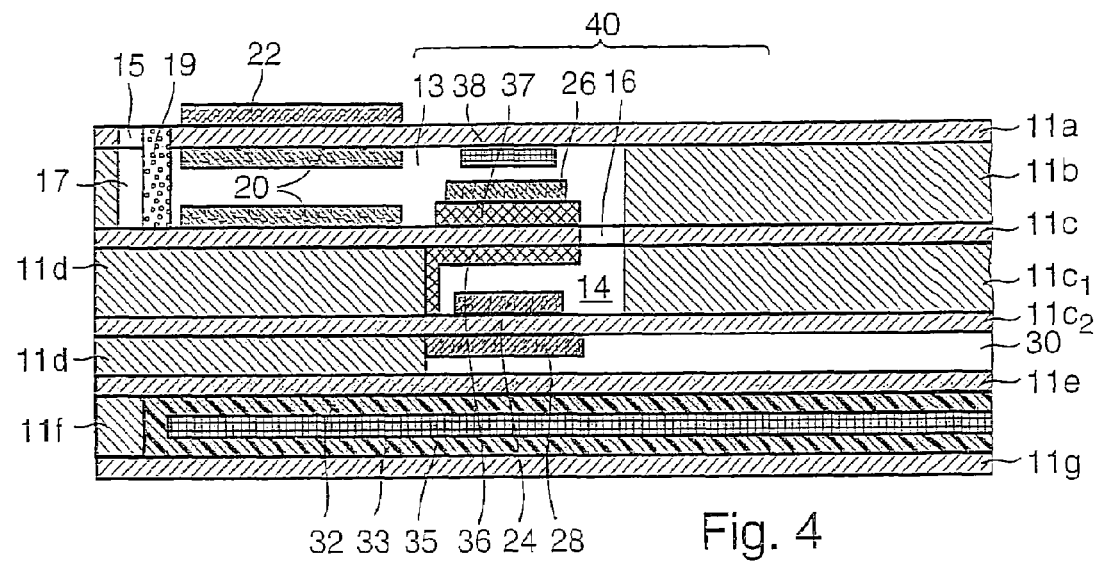
FIG. 4 shows a cross section through the large surface of a sensor element according to a third variant of the first exemplary embodiment, the second first means being situated in a separate layer plane of the gas sensor.

In FIGS. 2, 3 and 4 variants of the sensor element shown in FIG. 1 are illustrated. In the variant shown in FIG. 2, second inner pump electrode 24 as well as protective device 36 are shifted to the part of sensitive region 40 of the sensor element that faces away from gas intake port 15. By contrast, catalyst 38 and third inner pump electrode 26 are situated on the side of sensitive region 40 facing gas intake port 15. Since, in this variant, the gas component to be measured in sensitive region 40 immediately comes into contact with catalyst 38, without first passing second inner pump electrode 24, the probability is very low that the gas component to be measured in an undesired manner reaches second inner pump electrode 24 without being converted at catalyst 38. A sufficient availability of the reaction gas is ensured in this variant too, since the additional gas component is able to advance without hindrance to second inner electrode 24.

A second variant of the sensor element according to the first specific embodiment is shown in FIG. 3. The sensor element includes two additional solid electrolyte layers 11c1, 11c2. In layer 11c1 there is a further measuring gas chamber 14, which is in contact with first measuring gas chamber 13 via a cut through solid electrolyte layer 11c. Included in second measuring gas chamber 14 are catalyst 38 and third pump electrode 26. This layout of the sensor element effects an extending of the diffusion path within sensitive region 40 of the sensor element, without the sensor element having to be lengthened at the same time. The longer diffusion path effects a decoupling of the production of the reactive gas from its reaction with the gas component to be measured and from the detection of the residual content of the reaction gas.

FIG. 4 shows a third variant of the sensor element according to a first specific example. Its construction has the layer sequence of the sensor element shown in FIG. 3. Second inner pump electrode 24 as well as protective device 36 in this variant are located in second measuring gas chamber 14, and catalyst 38 and third pump electrode 26 are situated in first measuring gas chamber 13. This variant combines the advantages of the first variant according to FIG. 2 with the advantages of the second variant according to FIG. 3. The fact that the gas component to be measured in sensitive region 40 immediately reaches catalyst 38, without first passing second inner pump electrode 24, and the extended diffusion path between catalyst 38 and second inner electrode 24 minimize the probability that the gas component to be measured is able to reach second inner electrode 24.

Figure 5:
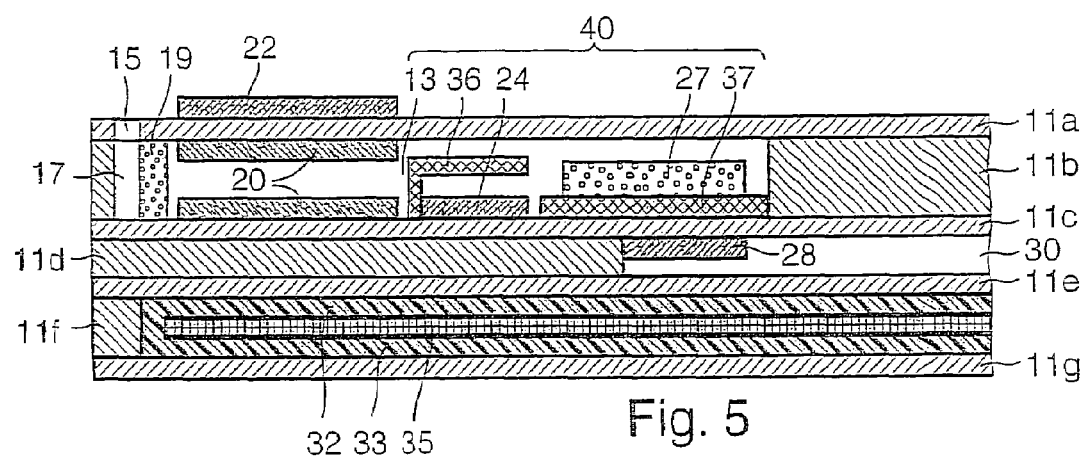
FIG. 5 shows a cross section through the large surface of a sensor element according to a second exemplary embodiment of the present invention, in which the catalyst is integrated into the second means.

FIG. 5 shows a sensor element according to a second specific embodiment of the present invention. Instead of a catalyst 38 and a separate third inner electrode 26, the sensor element has a catalytically active, combination electrode 27 which may be porous. This is situated in the part of sensitive region 40 facing away from gas intake port 15. Combination electrode 27 may be designed in the form of an electrode partially or completely covered by a catalytically active layer, or may be made completely of a catalytically active, porous material. Combination electrode 27 has the advantage that the spatial separation of the reaction of the reaction gas with the gas component to be measured and the detection of the residual content of reaction gas is eliminated. In addition, with the aid of combination electrode 27, the reaction of reaction gases and gas components to be measured may even be catalyzed, which are not normally catalyzable using only a catalytically active material, but additionally require the application of a corresponding potential to the catalyst. Furthermore, it is advantageous that, when manufacturing a sensor element according to the second exemplary embodiment, in comparison to the variants described before, one processing step, which includes the application of a separate catalyst 38, is avoided.

One variant of the sensor element shown in FIG. 5 is analogous to the variant shown in FIG. 2, and undertakes an exchange of inner electrode 24, which produces reaction gas, and protective device 36 with combination electrode 27. Second inner pump electrode 24 and protective device 36 is consequently positioned in the part of sensitive region 40 of the sensor element that faces away from gas intake port 15. At the same time, combination electrode 27 is provided in the part of sensitive region 40 facing gas intake port 15. In this variant, the probability that the gas component to be measured comes into contact with second inner pump electrode 24, and is lost for the measurement, is minimized.

In a further variant of the sensor element shown in FIG. 5, which largely corresponds to the variant shown in FIG. 3, combination electrode 27 is shifted to a separate layer 11c1. Here too, there comes about an extension of the diffusion path between inner electrode 24 producing reaction gas and combination electrode 27, while at the same time the linear extension of the sensor element is maintained.

A third variant of the sensor element described in FIG. 5, analogous to the third variant of the first specific embodiment illustrated in FIG. 4, includes the positioning of second inner pump electrode 24 and protective device 38 in separate solid electrolyte layer 11c1. This variant combines the advantages of the two variants already described of the sensor elements shown in FIG. 5 with one another.

Figure 6:
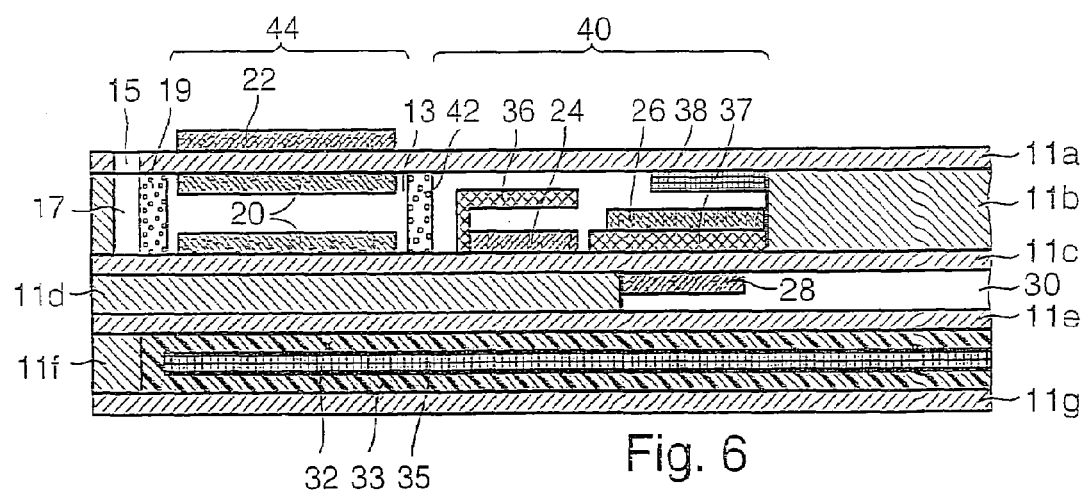
FIG. 6 shows a cross section through the large surface of a sensor element according to a third exemplary embodiment of the present invention, whose measuring gas chamber is subdivided by a diffusion barrier.

FIG. 6 illustrates a sensor element according to a third exemplary embodiment of the present invention, in which the measuring gas chamber 13 additiuonally includes a diffusion barrier 42, which subdivides measuring gas chamber 13 into region 44, regulating the oxygen content of the measuring gas and sensitive region 40. In the specific embodiments of the sensor element described so far, the possibility exists that reaction gas penetrates into the part of measuring gas chamber 13 facing gas intake port 15, in spite of protective device 36. In this context, if a reducing reaction gas is involved, it is converted because of the higher oxygen content in that location; if an oxidizing reaction gas is involved, it is decomposed at first inner electrode 20. Diffusion barrier 42 impedes an undesired diffusion of the reaction gas produced at second inner electrode 24 into the part of measuring gas chamber 13 facing gas intake port 15. This increases the measuring accuracy of the sensor element, since the concentration of the reaction gas produced is dependent, in sensitive region 40 of the sensor element only upon the quantity diffusing in of the gas component to be measured.

One variant of the sensor element shown in FIG. 6 exchanges the positions of inner electrodes 24, 26 and protective device 36 and catalyst 38, according to the sensor element shown in FIG. 2. Similar to that in FIG. 3, a further variant is based on the positioning of third inner electrode 26 and catalyst 38 in a separate layer plane 11c1. A third variant comes about, comparable to the variant shown in FIG. 4, because of the positioning of second inner electrode 24 and protective device 36 in second test electrolyte layer 11c1.

Figure 7:
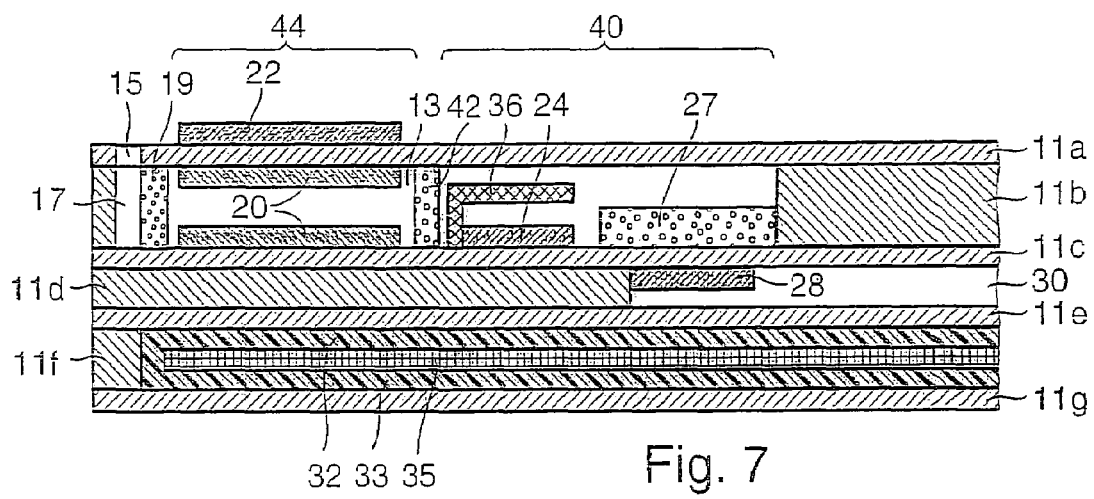
FIG. 7 shows a cross section through the large surface of a sensor element according to a fourth exemplary embodiment of the present invention, whose measuring gas chamber is subdivided by a diffusion barrier and in which the catalyst is integrated into the second means.

FIG. 7 shows a sensor element according to a fourth embodiment of the present invention. The sensor element shown in FIG. 7 combines the advantages of features of the second with those of the third exemplary embodiment. It includes both a diffusion barrier 42 between oxygen regulating and sensitive region 40, 44 of measuring gas chamber 13 and the combination of catalyst 38 and third inner electrode 26 to form combination electrode 27. Here too, an exchange of the positions of second inner electrode 24 and protective device 36 and combination electrode 27 is possible, as well as the shifting of combination electrode 27 or second inner electrode 24 into a separate layer plane 11c1.

Figure 8:
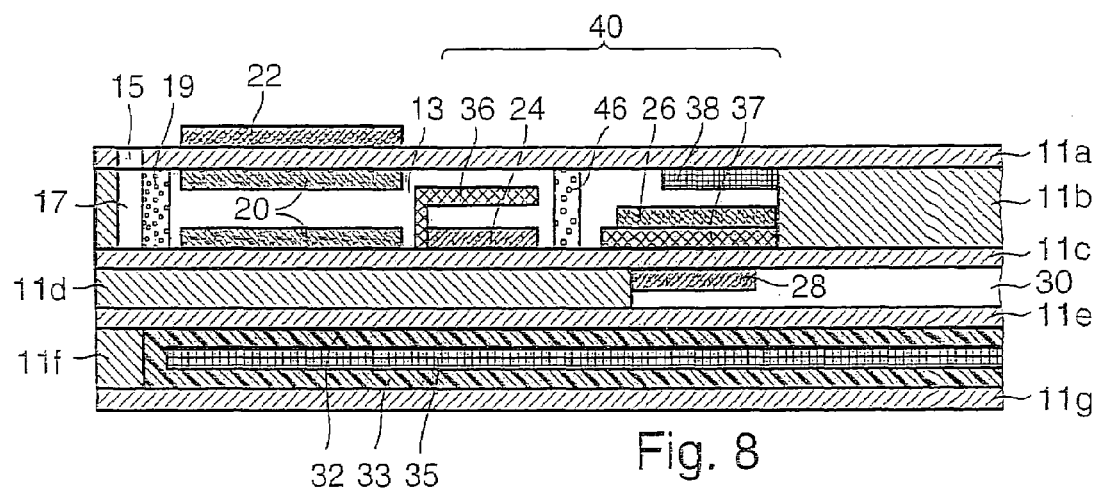
FIG. 8 shows a cross section through the large surface of a sensor element according to a fifth exemplary embodiment of the present invention, in which the diffusion barrier for subdividing the measuring gas chamber is situated between the first and second means.

FIG. 8 shows a sensor element according to a fifth embodiment of the present invention. The sensor element shown in FIG. 8 is based on the sensor element shown in FIG. 6, and inside measuring gas chamber 13 it has a diffusion barrier 46 which is connected downstream from second inner pump electrode 24, in the flow direction of the gas mixture, and subdivides sensitive region 40 spatially into a part facing gas intake port 15 and a part facing away from gas intake port 15. Such an embodiment is considered, above all, for application cases in which the reaction gas produced is inert to oxygen, or rather, is not subject to any decomposition at first inner electrode 20. On account of diffusion barrier 46, diffusion to catalyst 38 and to third inner electrode 26 is made more difficult, so that the effect of an extended diffusion path between second and third inner electrodes 24, 26 is made even more difficult.

Figure 9:
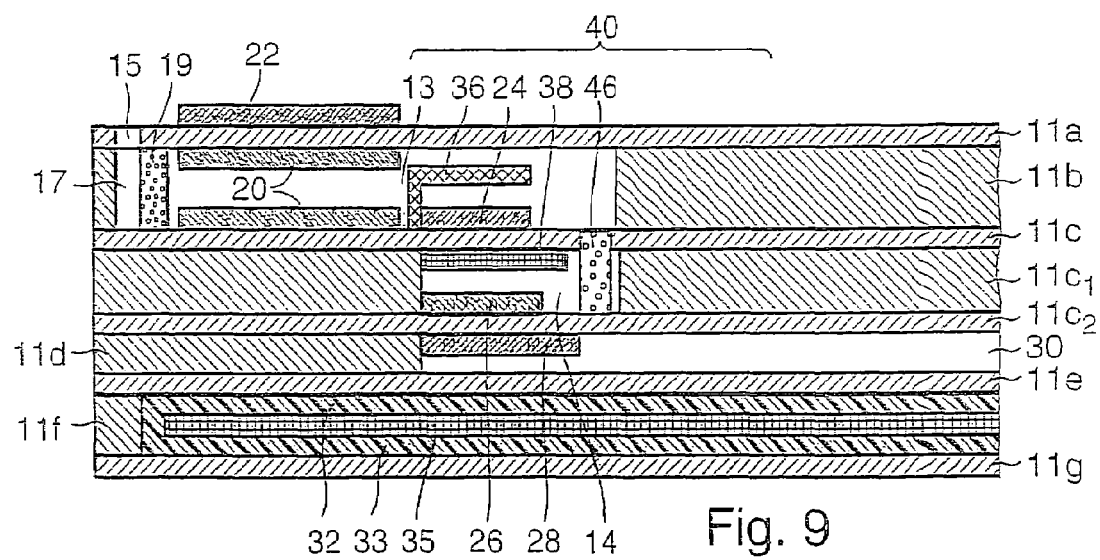
FIG. 9 shows a cross section through the large surface of a sensor element according to a first variant of the fifth exemplary embodiment, the second means and the catalyst being situated in a separate layer plane of the gas sensor.

If in addition, as shown in FIG. 9, catalyst 38 and third inner pump electrode 26 are moved into a separate layer plane 11c1, according to this first variant of the fifth exemplary embodiment, the effect of a diffusion made more difficult is further reinforced by the application of diffusion barrier 46 in breakthrough 16 of solid electrolyte layer 11c. The difficulty in diffusion leads to the elimination of inhomogeneities within the gas mixture.

A further variant is to combine catalyst 38 and third inner electrode 26 to form a combination electrode 27, which, for example, may be shifted into separate layer plane 11c1, just as was second inner electrode 24.

Variations in the sensor element on which the present invention is based, while maintaining the measuring principle, are also the subject matter of the present invention. Thus, measuring gas chamber 13, 14 may optionally be filled with porous material as the diffusion resistor, or it may include a plurality of diffusion barriers. In addition, more than one electrochemical cell for regulating the oxygen content of the measuring gas may be provided, or more than one electrochemical cell for producing a reducing or oxidizing reaction gas may be provided, respectively. The means used for determining the residual content of the reaction gas may also be provided in a plurality of designs.

The detection of the residual content of reaction gas in the gas mixture is performed using current measurements, in the case of the exemplary embodiments described, using the third pump cell. However, it is possible to make the detection using voltage measurements ("potentiometric"), using a concentration cell. To do this, third inner electrode 26 may be connected together with reference electrode 28 to form a Nernst cell or a concentration cell.

Figure 10:
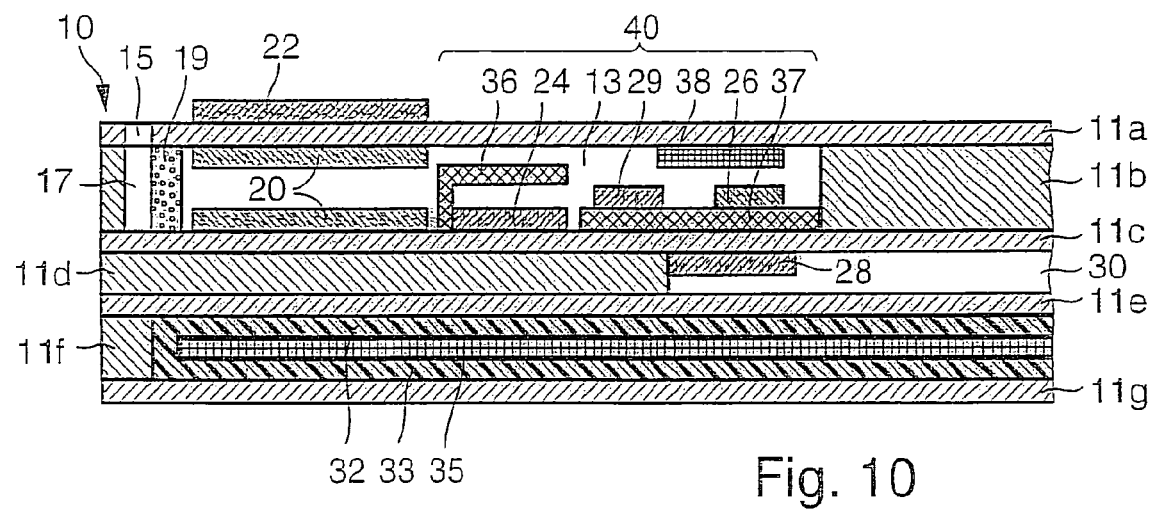
FIG. 10 shows a cross section through the large surface of a sensor element according to a sixth exemplary embodiment of the present invention, in which the determination of the gas component to be measured is made in a potentiometric manner.

The potentiometric detection of reaction gases, such as hydrogen or carbon monoxide is made particularly advantageously by using a so-called disequilibrium sensor. Such a sensor element is represented in FIG. 10. In measuring gas chamber 13 there is additionally a fourth inner electrode 29, which is catalytically inactive, and which is connected together with catalytically active third inner electrode 26 to form a Nernst cell or a concentration cell. Since at catalytically active third inner electrode 26 a different potential develops than at catalytically inactive fourth inner electrode 29, a voltage may be ascertained as a measuring signal. This effect is especially pronounced if a combination electrode 27 is used as the third inner electrode, while catalyst 38 is omitted.

Figure 11:
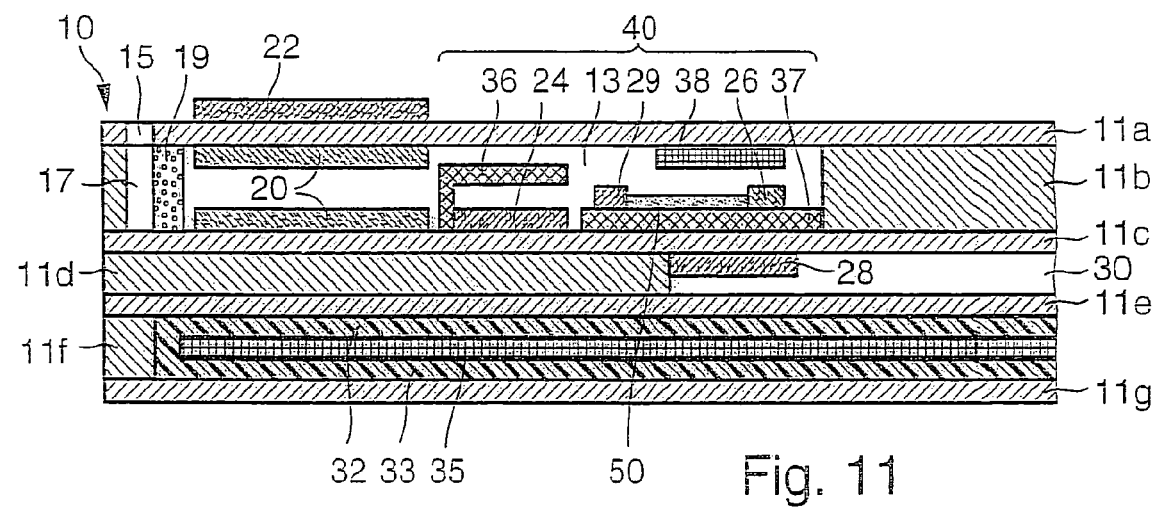
FIG. 11 shows a cross section through the large surface of a sensor element according to a seventh exemplary embodiment of the present invention, in which the determination of the gas component to be measured is made in a resistive manner.

A further possibility for detecting the reaction gas is by using a resistive measuring element. A corresponding exemplary embodiment is represented in FIG. 11. A voltage is applied to third and fourth electrodes 26, 29, and the resistance of a gas-sensitive layer 50 is determined between the two inner electrodes 26, 29.

Figure 12:
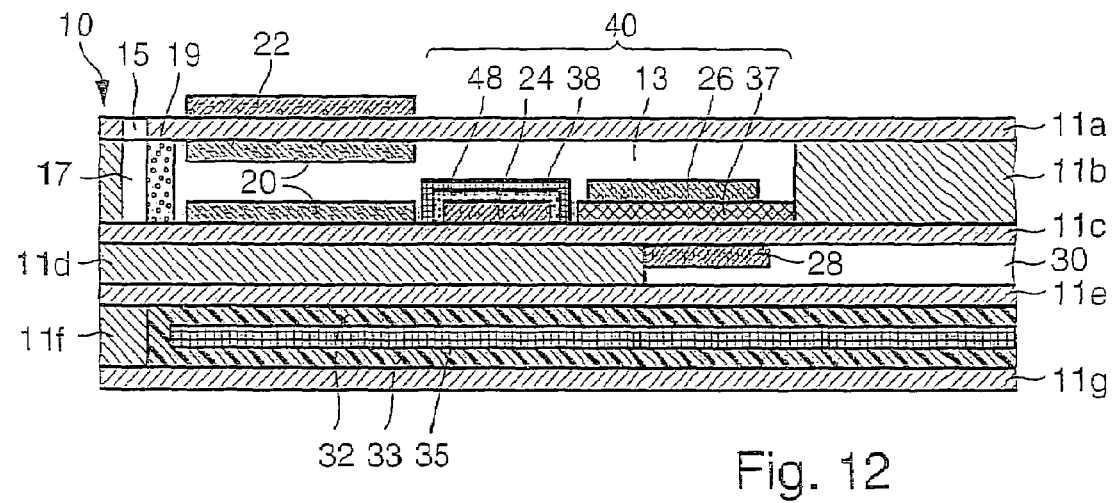
FIG. 12 shows a cross section through the large surface of a sensor element according to an eighth exemplary embodiment of the present invention, in which the catalyst is combined with the first means.

In an additional embodiment, according to FIG. 12, catalyst 38 is combined with second inner electrode 24. In this context, the catalyst may cover second inner electrode 24 partially or completely, and a porous solid electrolyte layer 48 may be positioned between catalyst 38 and the surface of second inner electrode 24, so as to prevent the gas component to be measured from being electrochemically converted at catalyst 38. The combination of catalyst 38 and second inner electrode 24 especially effectively prevents the access of the gas component to be measured to second inner electrode 24, since the gas component to be measured first has to pass porous catalyst 38 before it reaches second inner electrode 24. In catalyst 38 it meets an excess of reaction gas diffusing in the opposite direction, and is completely converted.

Figure 13:
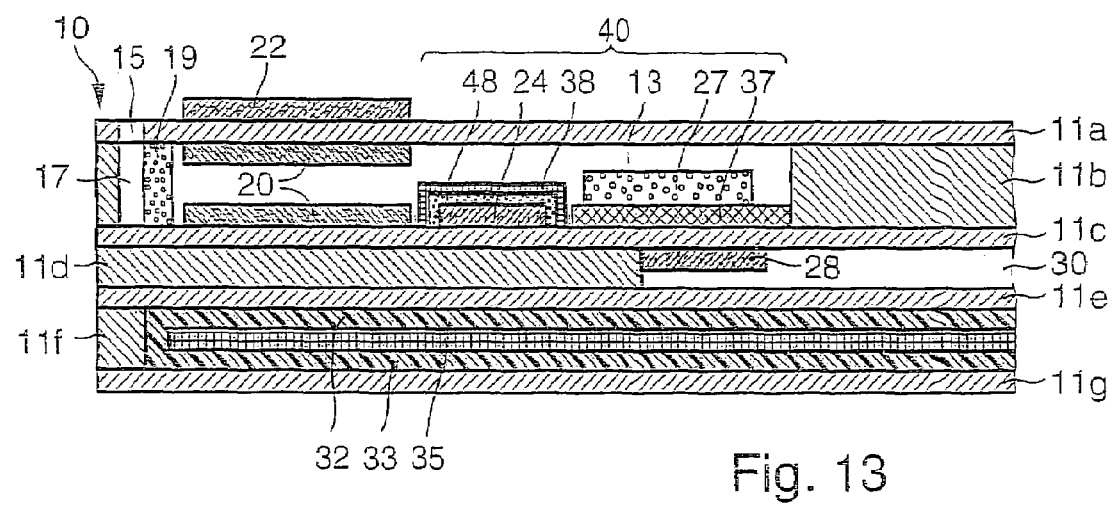
FIG. 13 shows a cross section through the large surface of a sensor element according to a ninth exemplary embodiment of the present invention, in which the catalyst is combined with the first and the second means.

FIG. 13 shows a sensor element according to a ninth exemplary embodiment. In this context, catalyst 38 is combined both with second inner electrode 24 and with third inner electrode 26. This arrangement leads to a particularly effective avoidance of the diffusion of the gas component to be measured to second inner electrode 24.

In order to ensure an especially favorable gas flow within the gas sensor, in addition to protective device 36, one or more devices may be provided for steering the gas flow within measuring gas chamber 13, 14.

Application possibilities of the gas sensor on which the present invention is based are to be seen, for example, in pollutant detection in the exhaust gases of internal combustion engines. In this regard, the detection of nitrogen oxides particularly makes possible control of, for instance, the service condition or the load state of an NOx storage catalyst. To do this, the gas sensor is mounted in an exhaust system branch, downstream in the flow direction from the NOx storage catalyst. In addition, the control of SCR systems operated using ammonia or urea is made possible by the determination of ammonia. In this context, the gas sensor is positioned in the exhaust system branch between the exhaust gas aftertreatment unit and the exhaust, and the ammonia content of the issuing exhaust gas is controlled.

The gas sensor according to the present invention may also be used for pollutant analysis in combustion systems used for heating purposes. In addition, there is the possibility of testing for the completeness of combustion by the detection, for instance, of methane.

Basically, the gas sensor according to the present invention makes possible both the purely qualitative detection of the existence of a gas component to be measured and the determination of its concentration in a gas mixture.

What is claimed is:

1. A gas sensor for measuring a first gas component in a gas mixture, having a solid electrolyte and at least one sensitive region, comprising:
a first means for generating a reaction gas in an amount in excess of the first gas component from a further gas component of the gas mixture; and
a second means situated in the sensitive region for determining a residual content of the reaction gas after a reaction that takes place between the reaction gas and the first gas component.

2. The gas sensor of claim 1, wherein the first means includes an electrochemical pump cell having an electrode facing the gas mixture.

3. The gas sensor of claim 2, wherein a constant current is applied to the electrode facing the gas mixture.

4. The gas sensor of claim 2, wherein at the electrode of the electrochemical pump cell facing the gas mixture, the further gas component includes at least one of water that is reduceable to hydrogen reaction gas and carbon dioxide that is reduceable to carbon monoxide reaction gas.

5. The gas sensor of claim 2, wherein at the electrode of the electrochemical pump cell facing the gas mixture, the further gas component includes at least one of nitrogen monoxide oxidizable to a reaction gas and a sulfur oxide oxidizable to a reaction gas.

6. The gas sensor of claim 1, wherein the second means for determining a residual content includes an electrochemical pump cell.

7. The gas sensor of claim 1, wherein the second means for determining a residual content includes an electrochemical concentration cell.

8. The gas sensor of claim 1, wherein the second means for determining a residual content includes a resistive measuring element.

9. The gas sensor of claim 1, further comprising:
a catalyst for catalyzing a reaction of the reaction gas with the first gas component.

10. The gas sensor of claim 9, wherein the catalyst is situated in direct proximity to the second means for determining a residual content.

11. The gas sensor of claim 9, wherein at least one of the first and second means includes an electrode and the catalyst substantially covers the electrode of the at least one of the first and the second means.

12. The gas sensor of claim 11, further comprising:
an electrochemical pump cell for regulating an oxygen proportion in the gas mixture, the electrochemical pump cell being connected to at least one of the first and the second means.

13. The gas sensor of claim 12, wherein the electrochemical pump cell includes a first electrode and a second electrode for regulating the oxygen proportion, the first electrode and the second electrode being situated in a different layer plane of the gas sensor from at least one of the catalyst and the electrodes of the first means and the second means.

14. The gas sensor of claim 12, further comprising:
a diffusion resistor; and
a measuring gas chamber surrounded by solid electrolyte layers, wherein the gas mixture is supplied to the measuring gas chamber via the diffusion resistor, and wherein at least one of the electrode of the first means, the electrode of the second means, the electrode of the electrochemical pump cell for regulating the oxygen proportion and the catalyst is located.

15. The gas sensor of claim 14, wherein the measuring gas chamber is subdivided into two regions, and wherein a diffusion barrier is provided between the two regions.

16. The gas sensor of claim 1, further comprising:
a third means for steering the gas mixture.

17. A method for measuring at least a first component of a gas mixture using a gas sensor, comprising:

producing a first reaction gas in an amount in excess of the first component of the gas mixture from a further component of the gas mixture;

reacting the first reaction gas with the first component;

determining a residual content of the first reaction gas after the reaction; and determining, from the residual content of the first reaction gas, an original concentration of the first component of the gas mixture.

18. The method of claim 17, wherein the first reaction gas is produced from the further component of the gas mixture by one of reduction and oxidation.

19. The method of claim 18, wherein the first reaction gas is produced from the further component of the gas mixture in an inner region of the gas sensor substantially separated from a gas chamber surrounding the gas sensor.

20. The method of claim 17, further comprising:
producing the first reaction gas in at least one of stoichiometric and volumetric excess with respect to the quantity of the first gas component.

21. The method of claim 17, further comprising:
determining an oxygen content of the gas mixture.

22. The method of claim 17, wherein a concentration of a gas component in the exhaust gas of an internal combustion engine is measured.

23. The method of claim 22, wherein the gas component includes at least one of nitrogen oxides and ammonia.

24. The method of claim 22, wherein at least one of a service condition and a load state of an NOx storage catalyst is measured.

25. A method for measuring at least a first component of a gas mixture and a second component of the gas mixture using a gas sensor, comprising:

producing a first reaction gas from a further component of the gas mixture;

reacting the first reaction gas with the first component;

determining a residual content of the first reaction gas after the reaction; and determining, from the residual content of the first reaction gas, an original concentration of the first component of the gas mixture; and producing a second reaction gas by oxidation for determining the second gas component:

wherein the first reaction gas is produced from the further component of the gas mixture by one of reduction and oxidation;

wherein the first reaction gas is produced from the further component of the gas mixture in an inner region of the gas sensor substantially separated from a gas chamber surrounding the gas sensor; and wherein the first reaction gas is produced by reduction for determining the first gas component.

* * * * *